United States Patent
Matsuura

(10) Patent No.: US 9,606,243 B2
(45) Date of Patent: Mar. 28, 2017

(54) RADIATION IMAGING APPARATUS, METHOD OF DETERMINING RADIATION IRRADIATION, AND STORAGE MEDIUM

(71) Applicant: CANON KABUSHIKI KAISHA, Tokyo (JP)

(72) Inventor: Tomohiko Matsuura, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/704,917

(22) Filed: May 5, 2015

(65) Prior Publication Data

US 2015/0331116 A1    Nov. 19, 2015

(30) Foreign Application Priority Data

May 16, 2014 (JP) ................................. 2014-102727
Jan. 8, 2015 (JP) ................................. 2015-002598

(51) Int. Cl.
*G01T 1/17* (2006.01)
*G01T 7/00* (2006.01)
*A61B 6/00* (2006.01)

(52) U.S. Cl.
CPC .............. *G01T 1/17* (2013.01); *A61B 6/4216* (2013.01); *A61B 6/4233* (2013.01); *A61B 6/4266* (2013.01); *A61B 6/54* (2013.01); *G01T 7/005* (2013.01)

(58) Field of Classification Search
CPC .............. G01T 1/16; G01T 1/17; G01T 7/005
See application file for complete search history.

(56) References Cited

U.S. PATENT DOCUMENTS

| 2011/0220802 A1* | 9/2011 | Frisch | G01T 1/208 250/363.03 |
|---|---|---|---|
| 2013/0193333 A1* | 8/2013 | Oda | G01T 1/24 250/370.08 |
| 2013/0208852 A1* | 8/2013 | Koishi | A61B 6/032 378/19 |
| 2013/0320224 A1 | 12/2013 | Sato | |

FOREIGN PATENT DOCUMENTS

| EP | 2720453 A2 | 4/2014 |
|---|---|---|
| JP | H11-299774 A | 11/1999 |
| JP | 2011-185622 A | 9/2011 |
| JP | 2012-083307 A | 4/2012 |
| JP | 2013-219408 A | 10/2013 |

OTHER PUBLICATIONS

European Search Report issued in corresponding application No. 15166340.8 on Oct. 7, 2015.

* cited by examiner

*Primary Examiner* — David Porta
*Assistant Examiner* — Faye Boosalis
(74) *Attorney, Agent, or Firm* — Carter, DeLuca, Farrell & Schmidt, LLP

(57) ABSTRACT

A radiation imaging apparatus includes a plurality of detection apparatuses configured to output image data based on radiation. The apparatus includes measurement units configured to respectively measure radiation detection levels in the plurality of detection apparatuses; and an irradiation determination unit configured to determine presence/absence of radiation irradiation based on the measured detection levels.

23 Claims, 7 Drawing Sheets

RADIATION IMAGING APPARATUS, METHOD OF DETERMINING RADIATION IRRADIATION, AND STORAGE MEDIUM

BACKGROUND OF THE INVENTION

Field of the Invention

The present invention relates to a radiation imaging apparatus, a method of determining radiation irradiation, and a storage medium.

Description of the Related Art

Recently, an FPD (flat panel detector) has been put into practical use. In this FPD, a phosphor is arranged on a TFT active matrix substrate, and radiation is accumulated as a charge signal and converted into a digital signal, thereby providing a diagnostic image.

If the FPD is used as the imaging medium of a modality, it may become difficult to establish an interface between a radiation generation apparatus and the FPD. As a method to cope with this, for example, Japanese Patent Laid-Open Nos. 2012-083307 and 2011-185622 propose an FPD which detects the start of radiation irradiation on an FPD side and automatically starts an accumulation operation without providing an interface between a radiation generation apparatus and the FPD.

For example, Japanese Patent Laid-Open No. 2012-083307 proposes a technique of controlling a threshold based on a TFT temperature at the time of selecting an imaging menu, and Japanese Patent Laid-Open No. 2011-185622 proposes a technique of controlling a threshold based on a VS signal value at the time of a reset operation.

In the method of setting the threshold according to each conventional technique, a uniform threshold is set even if a plurality of FPDs (detection apparatuses) are used. For this reason, if the characteristics of the detection apparatuses change locally due to an external environment, it exerts an influence on the detection accuracy of all the plurality of detection apparatuses, and thus the improvement of the detection accuracy of detecting the presence/absence of radiation irradiation is limited.

The present invention provides a technique capable of detecting the presence/absence of radiation irradiation appropriately even if the external environment changes locally.

SUMMARY OF THE INVENTION

According to one aspect of the present invention, there is provided a radiation imaging apparatus which includes a plurality of detection apparatuses configured to output image data based on radiation, the apparatus comprising: measurement units configured to respectively measure radiation detection levels in the plurality of detection apparatuses; and an irradiation determination unit configured to determine presence/absence of radiation irradiation based on the measured detection levels.

According to another aspect of the present invention, there is provided a radiation imaging apparatus comprising: an imaging unit configured to output charge information corresponding to radiation; measurement units configured to respectively measure radiation detection levels in a plurality of regions of the imaging unit; and an irradiation determination unit configured to determine presence/absence of radiation irradiation by comparing a threshold and the measured detection levels.

According to still another aspect of the present invention, there is provided a method of determining radiation irradiation in a radiation imaging apparatus which includes a plurality of detection apparatuses configured to output image data based on radiation, the method comprising: a step of respectively measuring radiation detection levels in the plurality of detection apparatuses; and a determination step of determining presence/absence of radiation irradiation based on the measured detection levels.

According to yet another aspect of the present invention, there is provided a method of determining radiation irradiation in a radiation imaging apparatus, the method comprising: a step of measuring radiation detection levels in a plurality of regions of an imaging unit which outputs charge information corresponding to radiation; and a step of determining presence/absence of radiation irradiation by comparing a threshold and the measured detection levels.

Further features of the present invention will become apparent from the following description of exemplary embodiments (with reference to the attached drawings).

DESCRIPTION OF THE EMBODIMENTS

A radiation imaging apparatus according to each embodiment will be described in detail below with reference to the accompanying drawings. Note that an FPD using a photodiode will be described below as an example. However, the present invention can also be applied to a direct FPD which directly converts radiation into electrons.

First Embodiment

Figure 1:
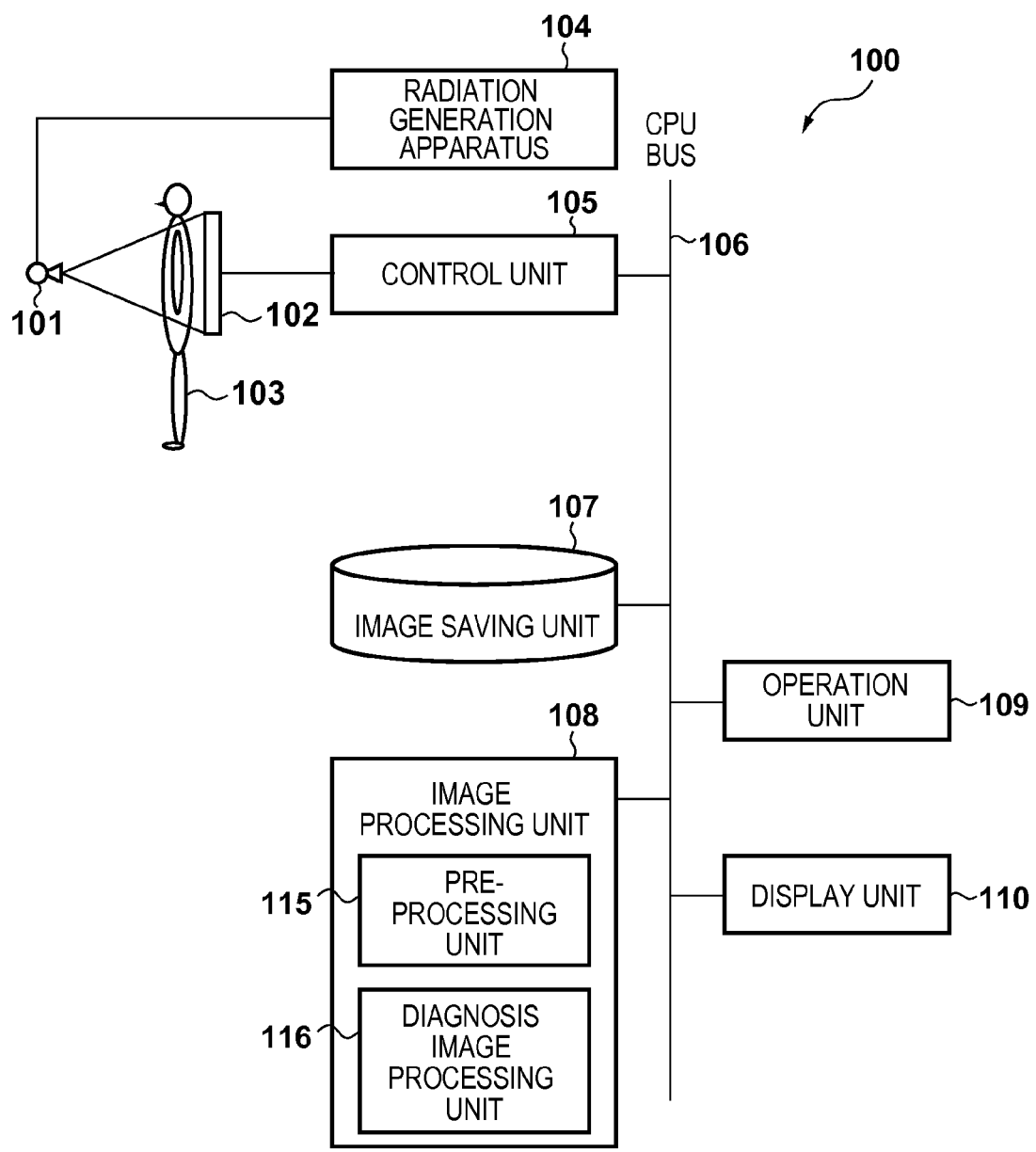
FIG. 1 is a diagram showing the functional arrangement of a radiation imaging apparatus according to the first embodiment.

FIG. 1 is a diagram showing the functional arrangement of a radiation imaging apparatus 100 according to the first embodiment. A radiation generator 101 of the radiation imaging apparatus 100 irradiates an object 103 with radiation. Upon pressing an emission switch, a radiation generation apparatus 104 gives the radiation generator 101a high-voltage pulse and generates radiation. A control unit 105 controls an FPD 102 (detection unit) so as to convert, by a phosphor, radiation that has passed through the object 103 into visible light and detect an electrical signal by a photodiode. The detected electrical signal is A/D-converted into digital data and transmitted to the control unit 105 as image data.

The control unit 105 is connected to a CPU bus 106 of one or a plurality of computers. In addition, an image saving unit 107, an image processing unit 108, an operation unit 109, and a display unit 110 are connected to the CPU bus 106. Furthermore, a CPU (Central Processing Unit), a ROM (Read Only Memory), a RAM (Random Access Memory), a graphic control unit, a network communication unit, and the like included in a general computer are also connected to the CPU bus 106. The CPU executes a program stored in the ROM or the RAM, thereby controlling the entire computer.

The image processing unit 108 includes a pre-processing unit 115 and a diagnosis image processing unit 116. The pre-processing unit 115 can perform pre-processing such as offset correction, sensitivity correction, pixel correction, and the like to correct characteristic variations in the solid-state image sensors of the FPD. The diagnosis image processing unit 116 can perform diagnosis image processing such as tone processing, dynamic range processing, spatial frequency processing, and the like.

The display unit 110 displays, on a monitor, the image data processed by the image processing unit 108. The operation unit 109 inputs instructions to the image processing unit 108 and the control unit 105. The image saving unit 107 saves the digital signal output from the control unit 105 and the image data processed by the image processing unit 108.

Figure 2:
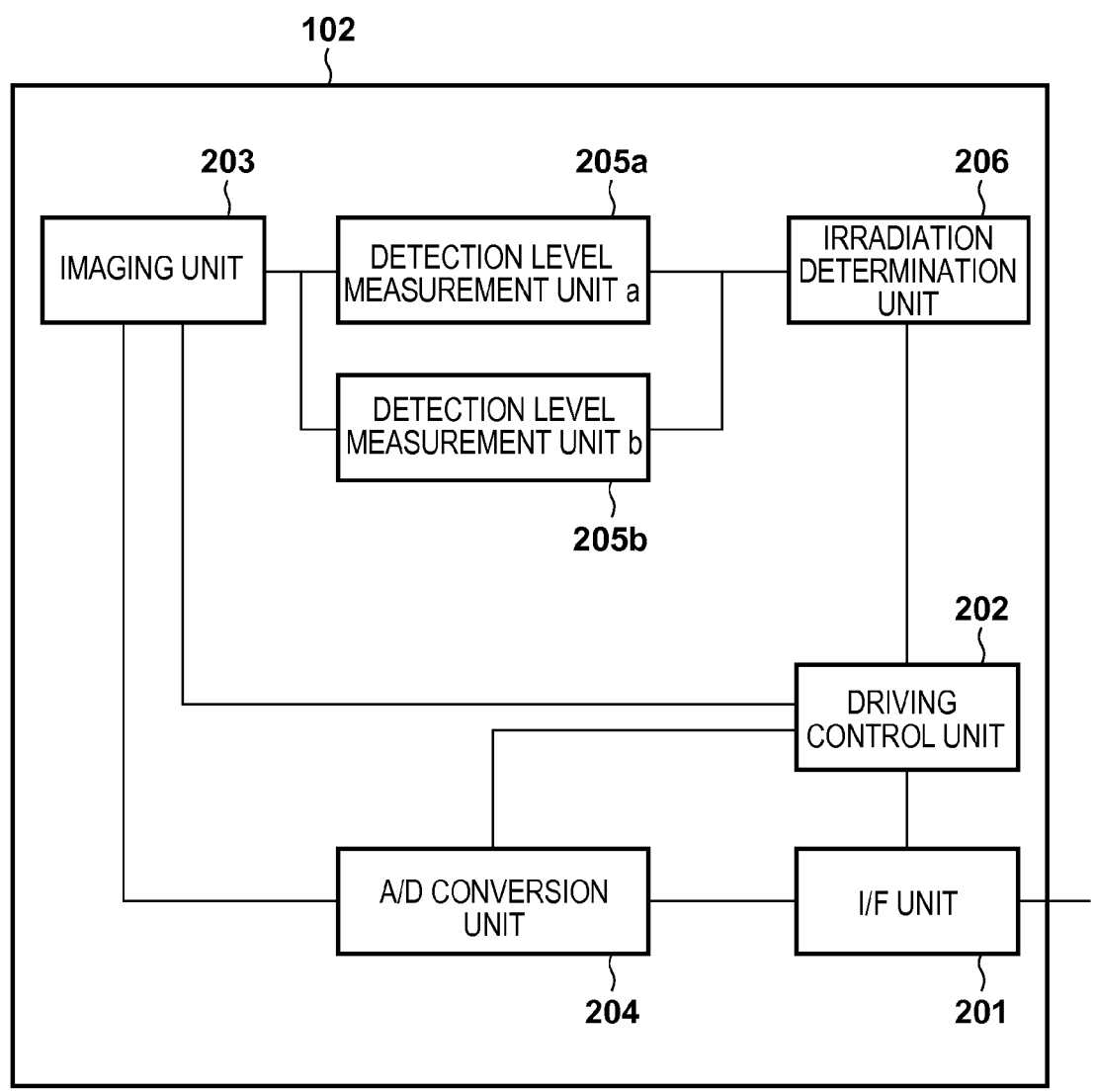
FIG. 2 is a block diagram showing the functional arrangement of an FPD according to the first embodiment.

The functional arrangement of the FPD 102 will now be described. FIG. 2 is a block diagram showing the functional arrangement of the FPD 102. An I/F unit 201 (interface unit) is connected to the control unit 105 to receive a control signal and transmit the image data.

The radiation imaging apparatus according to this embodiment includes the FPD 102 (detection unit) which detects radiation. The FPD 102 of the radiation imaging apparatus includes an imaging unit 203 which outputs pieces of charge information corresponding to radiation. The FPD 102 of the radiation imaging apparatus also includes measurement units (a detection level measurement unit 205a and a detection level measurement unit 205b) which respectively measure radiation detection levels in a plurality of regions of the imaging unit using the pieces of charge information, and a irradiation determination unit 206 which determines the presence/absence of radiation irradiation by comparing a threshold and the respectively measured detection levels. Also, the FPD 102 (detection unit) of the radiation imaging apparatus further includes a driving control unit 202 which controls, in accordance with a determination result by the irradiation determination unit, the imaging unit which outputs the pieces of charge information corresponding to radiation. Note that the plurality of regions of the imaging unit differ from each other. The measurement units include the plurality of detection level measurement units (the detection level measurement unit 205a and the detection level measurement unit 205b) which measure the detection levels in the different regions of the imaging unit.

As the arrangement of the measurement units, the single measurement unit may measure the radiation detection levels in the different regions of the imaging unit 203 using the pieces of charge information or the plurality of measurement units can measure the radiation detection levels in the different regions of the imaging unit 203 using the pieces of charge information. As the arrangement of the plurality of measurement units, an example of the arrangement in which the detection level measurement unit 205a (first detection level measurement unit) and the detection level measurement unit 205b (second detection level measurement unit) are used to measure the radiation detection levels will be described below.

The driving control unit 202 controls the operation of the imaging unit 203 based on the control signal received by the I/F unit 201 and the determination result by the irradiation determination unit 206 to be described later. An A/D conversion unit 204 generates image data by reading out charges accumulated in the solid-state image sensors of the imaging unit 203 as the electrical signal.

The measurement units (the detection level measurement unit 205a and the detection level measurement unit 205b) include the plurality of detection level measurement units which measure the detection levels in the different regions of the imaging unit 203. The detection level measurement unit 205a (first detection level measurement unit) and the detection level measurement unit 205b (second detection level measurement unit) connected to the imaging unit 203 measure the radiation detection levels.

The irradiation determination unit 206 compares the threshold and the plurality of detection levels measured by the plurality of detection level measurement units (the detection level measurement unit 205a and the detection level measurement unit 205b). Then, the irradiation determination unit 206 determines the presence/absence of radiation irradiation based on the plurality of detection levels and transfers the result to the driving control unit 202. The driving control unit 202 controls the imaging unit 203 in accordance with the comparison result.

A processing procedure in a method of determining radiation irradiation executed in the radiation imaging apparatus 100 will now be described with reference to FIG. 3. First, in step S301, the control unit 105 outputs an imaging preparation instruction based on an input from the operation unit 109 and the driving control unit 202 receives the imaging preparation instruction from the control unit 105 via the I/F unit 201 (interface unit). Upon receiving the imaging preparation instruction, the driving control unit 202 controls the imaging unit 203 to be in a standby state. This causes the FPD 102 to change to the standby state in which radiation from the radiation generator 101 can be imaged.

Next, in steps S302a and S302b, each of the detection level measurement unit 205a and the detection level measurement unit 205b measures a radiation irradiation detection level. Processing operations in steps S302a and S302b are performed in parallel.

In a method of measuring radiation, for example, the magnitude of the charge information (VS signal value) output from each solid-state image sensor which can accumulate the charges corresponding to radiation of the imaging unit 203 can be used as the detection level. Each of the detection level measurement unit 205a and the detection level measurement unit 205b can measure, as the charge information, the current value of a bias line output from the corresponding sensor (solid-state image sensor) which accumulates the charges and determine each detection level based on the current value.

In this embodiment, the detection level measurement unit 205a and the detection level measurement unit 205b measure the detection levels by setting the solid-state image sensors in spatially different regions as a target. The detection level measurement unit 205a and the detection level measurement unit 205b measure the radiation detection levels in the different regions at the same timing. The detection level measured by the detection level measurement unit 205a is represented as Vsa and the detection level measured by the detection level measurement unit 205b is represented as VSb.

Then, in step S303, the irradiation determination unit 206 performs, based on the detection levels VSa and VSb, determination processing (presence/absence determination processing of radiation irradiation) of whether radiation is emitted from the radiation generator 101.

The irradiation determination unit 206 determines the presence of radiation irradiation if the sum of the plurality of detection levels exceeds a threshold and determines the absence of radiation irradiation if the sum of the plurality of detections levels becomes equal to or smaller than the threshold. For example, the irradiation determination unit 206 can determine that radiation is emitted from the radiation generator 101 if the sum of the detection level VSa and the detection level VSb exceeds a threshold VSth that has been set separately. That is, if the relationship of the sum of the detection levels (VSa+VSb)>the threshold VSth is satisfied, the irradiation determination unit 206 determines that there is radiation irradiation. On the other hand, if the sum of the detection levels (VSa+VSb) the threshold VSth is obtained, the irradiation determination unit 206 can determine that there is no radiation irradiation.

Note that processing for determining the presence/absence of radiation irradiation is not limited to the above-described example. As determination processing of determining the presence/absence determination of radiation irradiation, the irradiation determination unit 206 can also execute, for example, a determination method in accordance with an algorithm shown in FIG. 4. This algorithm uses two thresholds VSth1 and VSth2 that have been set separately as the reference. The magnitude relationship between the two thresholds is VSth1 (first threshold)>VSth2 (second threshold).

High level (level HIGH) is defined if the radiation detection level exceeds VSth1 (first threshold). Further, medium level (level MID) is defined if the radiation detection level becomes equal to or smaller than VSth1 and exceeds VSth2 (second threshold). Furthermore, low level (level LOW) is defined if the radiation detection level becomes equal to or smaller than VSth2.

The irradiation determination unit 206 determines the presence of radiation irradiation if it determines that at least one of the plurality of detection levels exceeds the first threshold (if it is high level (level HIGH)). The irradiation determination unit 206 determines the presence of radiation irradiation if both of the plurality of detection levels exceed the second threshold (if they are medium level (level MID)). Then, the irradiation determination unit 206 determines the absence of radiation irradiation if one of the plurality of detection levels becomes equal to or smaller than the second threshold (if it is low level (level LOW)).

In step S401, the irradiation determination unit 206 determines whether at least one of the radiation detection levels VSa and VSb is high level (level HIGH). If at least one of VSa and VSb is high level (level HIGH) in determination in step S401 (YES in step S401), the irradiation determination unit 206 advances processing to step S404. In step S404, the irradiation determination unit 206 determines the presence of radiation irradiation as its determination result and terminates processing of FIG. 4. On the other hand, if at least one of VSa and VSb is not high level in determination in step S401 (NO in step S401), the irradiation determination unit 206 advances processing to step S402.

In step S402, the irradiation determination unit 206 determines whether both of VSa and VSb are medium level (level MID). If both of VSa and VSb are medium level in determination in step S402 (YES in step S402), the irradiation determination unit 206 advances processing to step S404. Then, in step S404, the irradiation determination unit 206 determines the presence of radiation irradiation as its determination result and terminates processing of FIG. 4. On the other hand, if neither VSa nor VSb is medium level in determination in step S402 (NO in step S402), the irradiation determination unit 206 advances processing to step S403. Then, in step S403, the irradiation determination unit 206 determines the absence of radiation irradiation as its determination result and terminates processing of FIG. 4.

Figure 3:
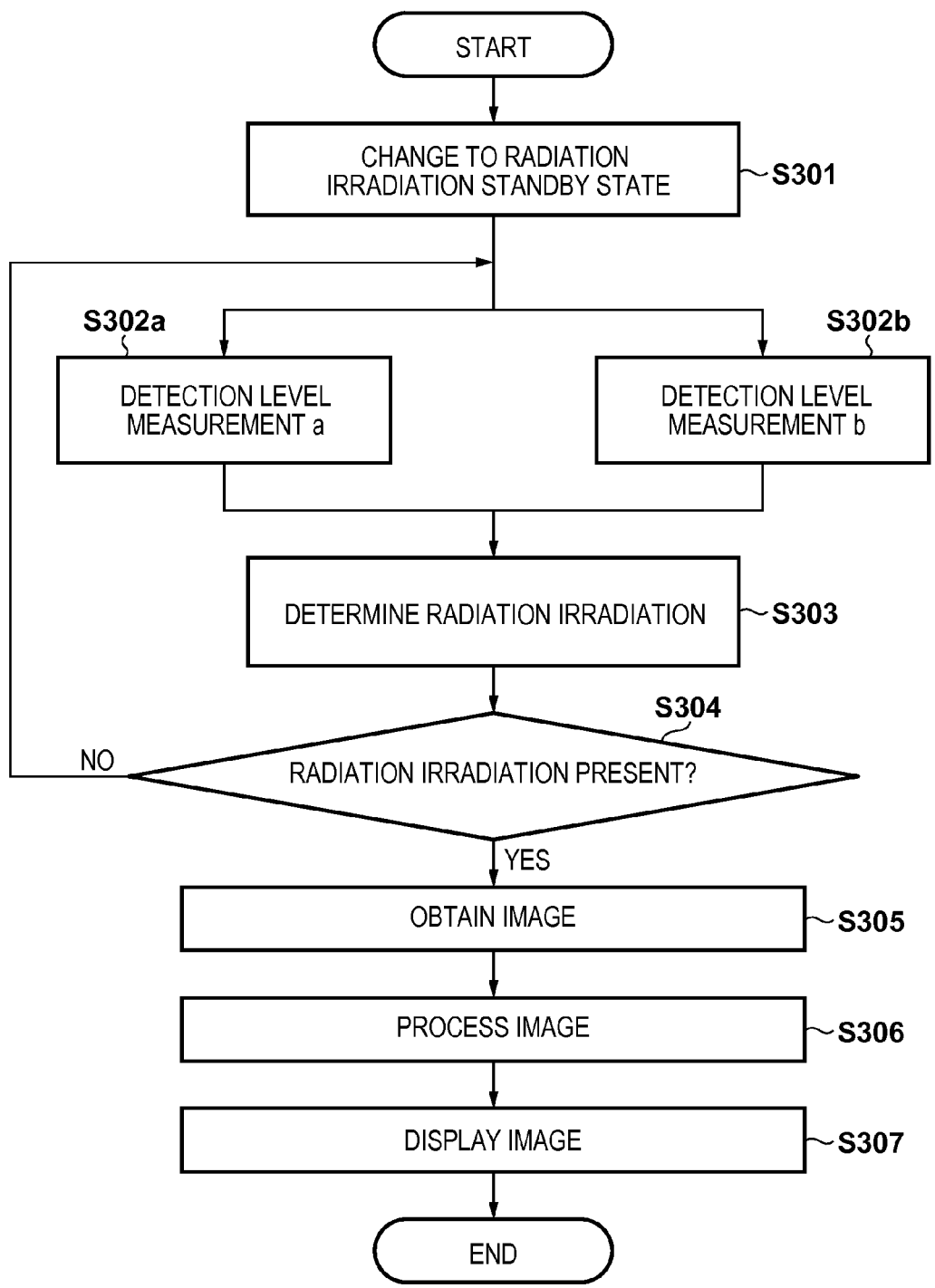
FIG. 3 is a flowchart for explaining a processing procedure according to the first embodiment.

Returning to the description of FIG. 3, in step S304, the driving control unit 202 receives, from the irradiation determination unit 206, the result of presence/absence determination processing of radiation irradiation. Then, the driving control unit 202 changes control contents in accordance with the result of presence/absence determination processing. If the irradiation determination unit 206 determines the absence of radiation irradiation, the driving control unit 202 controls the measurement units to continue measurement of the radiation irradiation detection levels. The driving control unit 202 returns processing to steps S302a and S302b, and continues measurement of the radiation irradiation detection levels (NO in step S304).

Then, in steps S302a and S302b, the detection level measurement unit 205a and the detection level measurement unit 205b measure the radiation irradiation detection levels. Unless the presence of radiation irradiation is determined, the radiation imaging apparatus 100 repeats processing in steps S302a, S302b, S303, and S304, and waits for radiation irradiation.

On the other hand, if the irradiation determination units 206 determines the presence of radiation irradiation in determination processing in step S304, the driving control unit 202 advances processing to step S305 (YES in step S304).

Then, in step S305, if the irradiation determination unit 206 determines the presence of radiation irradiation by comparison in step S303, the driving control unit 202 performs control for obtaining, from the imaging unit 203, an image based on the accumulated charges. That is, the driving control unit 202 controls the A/D conversion unit 204 in order to obtain the image based on the electrical signal of the charges. The A/D conversion unit 204 generates, under the control of the driving control unit 202, the image data by reading out the charges accumulated in the solid-state image sensors of the imaging unit 203 as the electrical signal. The image data generated by the A/D conversion unit 204 is transmitted to the control unit 105 via the I/F unit 201. The control unit 105 saves the received image data in the image saving unit 107 or the RAM (not shown).

Next, in step S306, the image processing unit 108 performs image processing on the image data stored in the image saving unit 107 or the RAM (not shown). The image processing unit 108 can perform, for example, pre-processing such as offset correction, sensitivity correction, pixel correction, and the like to correct the characteristic variations in the solid-state image sensors of the FPD, and diagnosis image processing such as tone processing, dynamic range processing, spatial frequency processing, and the like.

Then, in step S307, the display unit 110 displays, on the monitor, the image data which has undergone image processing by the image processing unit 108. Then, processing in the radiation imaging apparatus 100 ends.

Second Embodiment

In the radiation imaging apparatus 100 according to the first embodiment, the arrangement in which the single detection apparatus (detection device) and the control unit 105 are used has been described. In the second embodiment, a radiation imaging apparatus which includes a plurality of detection apparatuses outputting image data based on radiation will be described. The radiation imaging apparatus according to this embodiment includes, in the plurality of detection apparatuses which output the image data based on radiation, measurement units which respectively measure radiation detection levels in the plurality of detection apparatuses and irradiation determination units which determine the presence/absence of radiation irradiation based on the measured detection levels.

Figure 5:
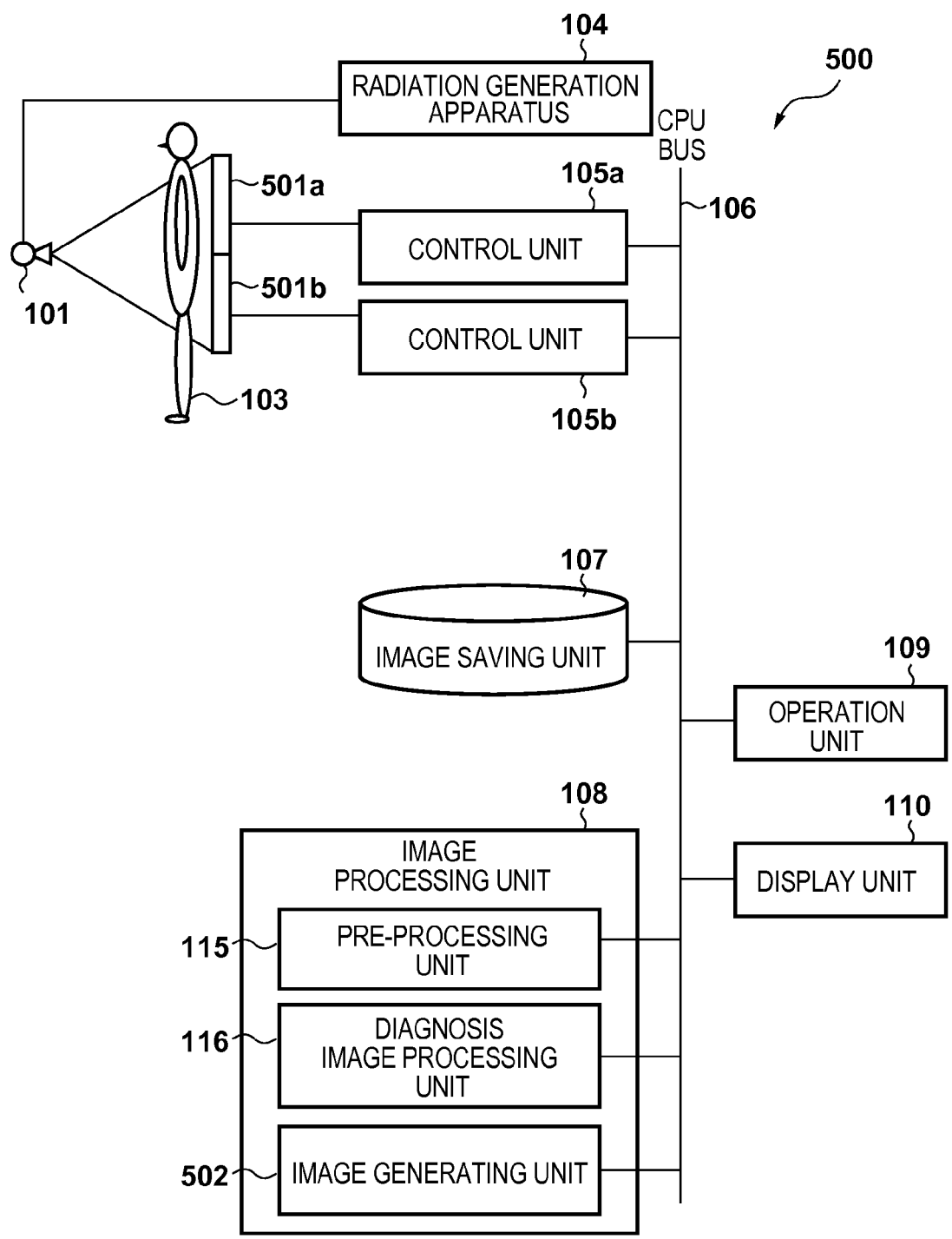
FIG. 5 is a diagram showing the functional arrangement of a radiation imaging apparatus according to the second embodiment.

FIG. 5 is a diagram showing the functional arrangement of a radiation imaging apparatus 500 according to the second embodiment. As an example of the arrangement of a plurality of FPDs (detection apparatuses), an example in which two FPDs 501a and 501b are used will be described. In addition, an arrangement in which two control units 105a and 105b are used in correspondence with the two FPDs 501a and 501b will be described as an example.

An image processing unit 108 includes an pre-processing unit 115, a diagnosis image processing unit 116, and an image generating unit 502. The pre-processing unit 115 and the diagnosis image processing unit 116 have the same arrangement as those described in the image processing unit 108 according to the first embodiment. The image generating unit 502 combines a plurality of image data generated by the plurality of detection apparatuses to generate one image data. That is, the image generating unit 502 combines the plurality of image data generated by A/D conversion units 204 of the plurality of FPDs (detection apparatuses) to generate one image (image data). The arrangement of the image processing unit according to this embodiment is different from the arrangement of the image processing unit 108 according to the first embodiment in that the image generating unit 502 is added.

The rest of the arrangement of the radiation imaging apparatus is the same as that of the radiation imaging apparatus 100 used in the first embodiment, and thus a repetitive description thereof will be omitted.

Figure 6:
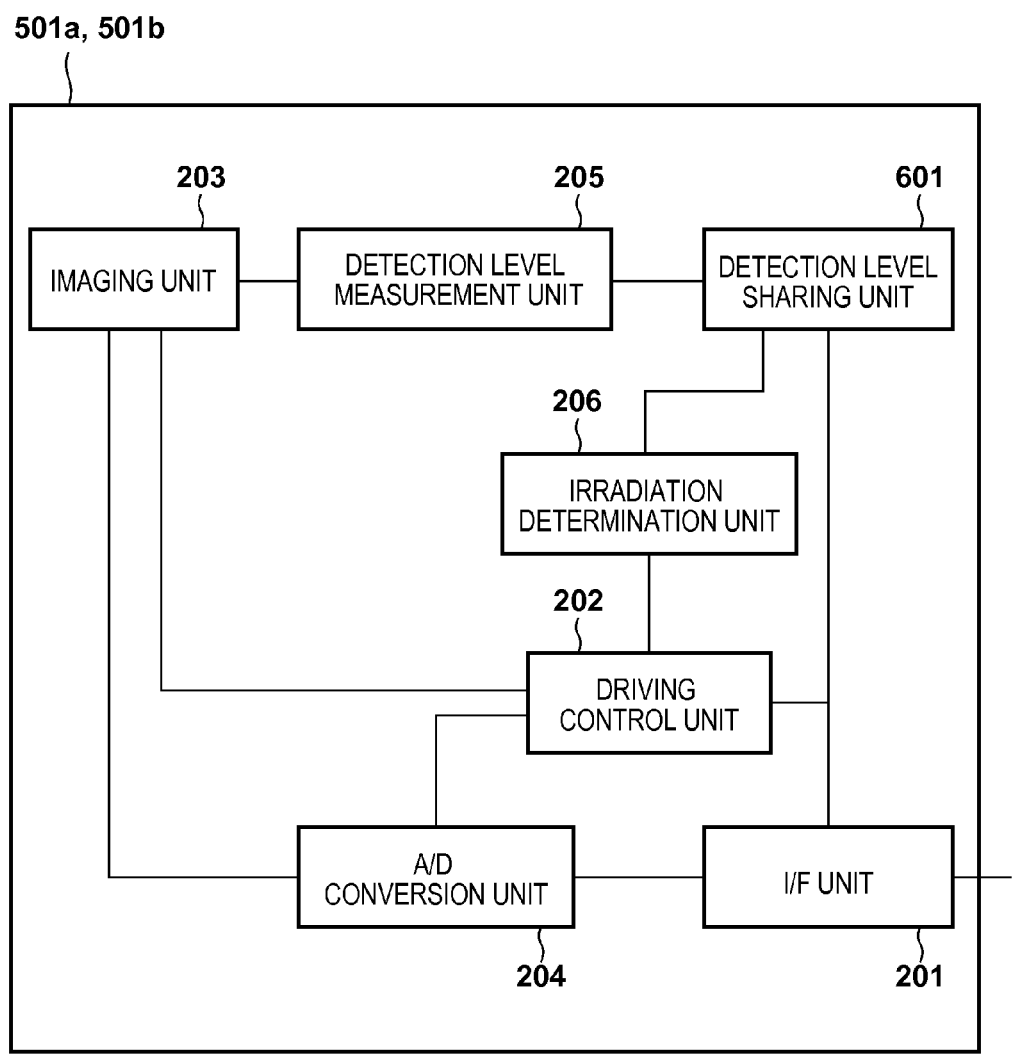
FIG. 6 is a block diagram showing the functional arrangement of FPDs according to the second embodiment.

The functional arrangement of the FPD 501a and the FPD 501b according to this embodiment will now be described. FIG. 6 is a block diagram showing the functional arrangement of the FPD 501a and the FPD 501b. The radiation imaging apparatus according to this embodiment includes the plurality of FPDs (detection apparatuses) which detect radiation (the FPD 501a and the FPD 501b). Each detection apparatus out of the plurality of FPDs (detection apparatuses) includes an imaging unit 203 which outputs charge information corresponding to radiation and a detection level measurement unit 205 (measurement unit) which measures a radiation detection level using charge information. Each detection apparatus also includes a detection level sharing unit 601 which obtains the radiation detection level measured in the other detection apparatus and an irradiation determination unit 206 which determines the presence/absence of radiation irradiation by comparing a threshold and the measured detection level. The irradiation determination unit 206 can determine the presence/absence of radiation irradiation by comparing the threshold, and the measured detection level and the detection level obtained from the other detection apparatus. For example, as the plurality of detection apparatuses, the FPD 501a is used as the first detection apparatus and the FPD 501b is used as the second detection apparatus. The detection level sharing unit 601 obtains and shares the radiation detection level measured in the first detection apparatus and the radiation detection level measured in the second detection apparatus. The irradiation determination unit 206 determines the presence/absence of radiation irradiation by comparing the threshold and the shared respective detection levels.

The detection level measurement unit 205 provided in each of the plurality of FPDs according to this embodiment measures the radiation detection level using the pieces of charge information in the plurality of detection apparatuses. The detection level sharing unit 601 provided in each of the plurality of FPDs performs processing (sharing processing) for sharing the radiation detection level between the other FPD. In sharing processing, each detection level sharing unit 601 outputs the detection level measured by the detection level measurement unit 205 and obtains the radiation detection level measured in the other detection apparatus.

Each detection level sharing unit 601 transmits (outputs), to a corresponding control unit, a measurement result of the detection level measured by the detection level measurement unit 205 via an I/F unit 201 (interface unit). At this time, each detection level sharing unit 601 inputs, to the irradiation determination unit 206, the measurement result of the detection level measured by the detection level measurement unit 205.

Each control unit communicates, via a CPU bus 106, the measurement result of the detection level between the other control unit which controls the other FPD. As a result of the communication, each control unit transmits the received measurement result of the detection level in the other FPD to the detection level sharing unit 601 via the I/F unit 201. Each detection level sharing unit 601 inputs, to the irradiation determination unit 206, the received (obtained) measurement result of the detection level in the other FPD. With above-described processing, the measurement result of the detection level by the detection level measurement unit 205 in each FPD is shared between the plurality of FPDs. Detailed processing will be described later with reference to FIG. 7.

The irradiation determination unit 206 determines the presence/absence of radiation irradiation based on the plurality of detection levels and transfers the result to a driving control unit 202. The arrangement of each of the imaging unit 203 and the A/D conversion unit 204 is the same as in the first embodiment, and thus a description thereof will be omitted.

Figure 7:
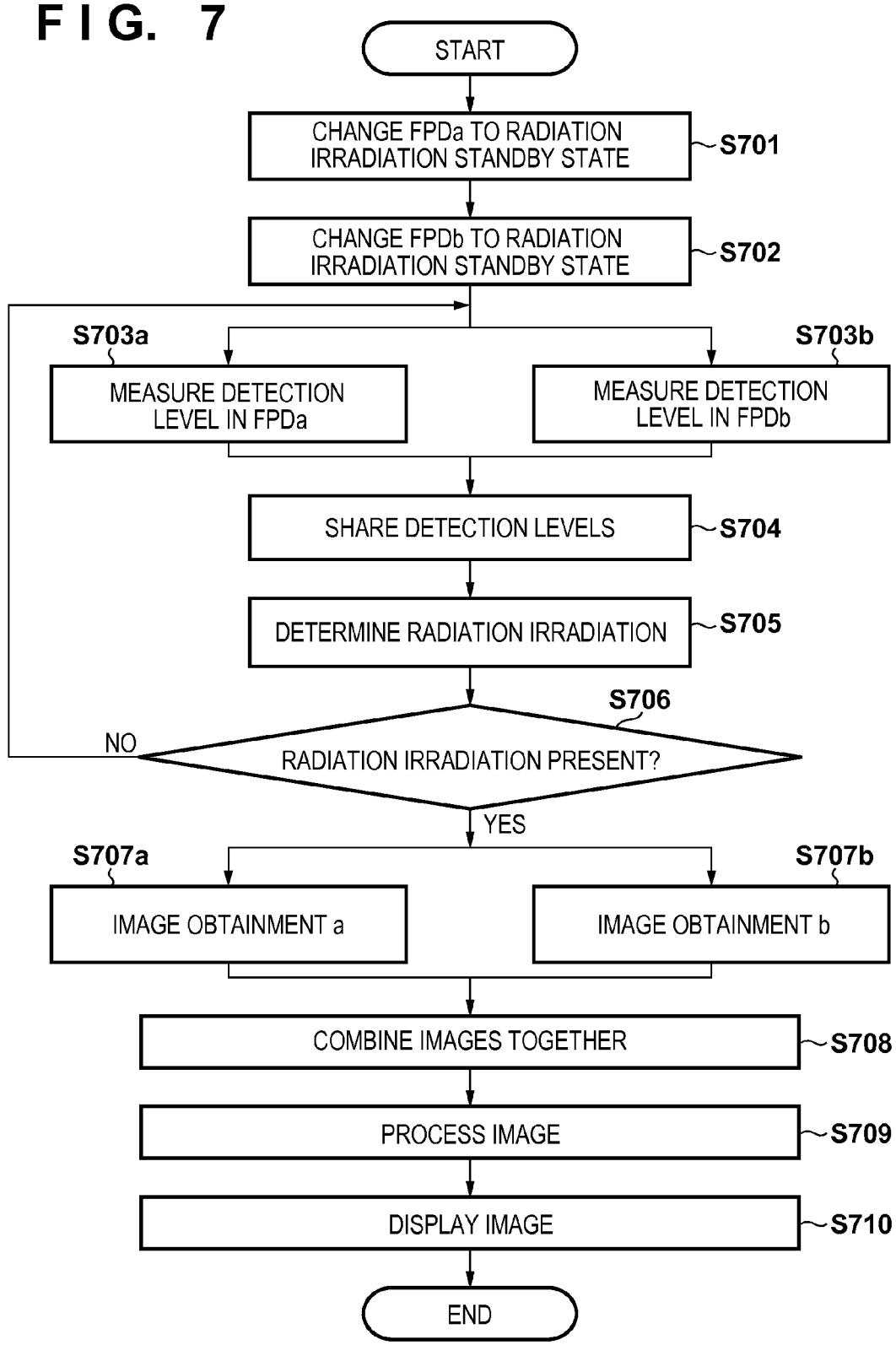
FIG. 7 is a flowchart for explaining a processing procedure according to the second embodiment.

A processing procedure in the radiation imaging apparatus 500 shown in FIGS. 5 and 6 will now be described with reference to FIG. 7.

First, in step S701, the control unit 105a sets the FPD 501a to a standby state based on an input from an operation unit 109. The control unit 105a outputs an imaging preparation instruction. The imaging preparation instruction from the control unit 105a is input to the driving control unit 202 via the I/F unit 201 (interface unit). Upon receiving the imaging preparation instruction, the driving control unit 202 controls the imaging unit 203 to be in the standby state. This causes the FPD 501a to change to the standby state in which radiation emitted from a radiation generator 101 can be imaged.

Next, in step S702, the control unit 105b sets the FPD 501b to the standby state based on the input from the operation unit 109. The control unit 105b outputs an imaging preparation instruction. The imaging preparation instruction from the control unit 105b is input to the driving control unit 202 via the I/F unit 201. Upon receiving the imaging preparation instruction, the driving control unit 202 controls the imaging unit 203 to be in the standby state. This causes the FPD 501b to change to the standby state in which radiation emitted from the radiation generator 101 can be imaged.

Then, in steps S703a and S703b, the detection level measurement unit 205 measures a radiation irradiation detection level in each of the FPDs (the FPD 501a and the FPD 501b). Processing operations in steps S703a and S703b are performed in parallel. A measurement method as in the first embodiment can be applied, and thus a detailed description thereof will be omitted to avoid a repetitive description. The detection level obtained by the detection level measurement unit 205 of the FPD 501a is represented as Vsa and the detection level obtained by the detection level measurement unit 205 of the FPD 501b is represented as VSb.

Then, in step S704, the detection level sharing units 601 perform sharing processing for sharing the detection levels VSa and VSb obtained by the respective FPDs.

The detection level sharing units 601 can perform the following processing as sharing processing. For example, the detection level sharing unit 601 of the FPD 501a transmits (outputs), to the control unit 105a via the I/F unit 201, the measurement result of the detection level measured by the detection level measurement unit 205 of the FPD 501a. At this time, the detection level sharing unit 601 inputs the measurement result of the measured detection level to the irradiation determination unit 206 of the FPD 501a.

Likewise, the detection level sharing unit 601 of the FPD 501b transmits (outputs), to the control unit 105b via the I/F unit 201, the measurement result of the detection level measured by the detection level measurement unit 205 of the FPD 501b. At this time, the detection level sharing unit 601 inputs the measurement result of the measured detection level to the irradiation determination unit 206 of the FPD 501b.

The control unit 105a transmits the measurement result of the detection level in the FPD 501a to the control unit 105b via the CPU bus 106. Also, the control unit 105b transmits the measurement result of the detection level in the FPD 501b to the control unit 105a via the CPU bus 106.

The control unit 105a receives the measurement result of the detection level in the FPD 501b transmitted from the control unit 105b. Then, the control unit 105a transmits the received measurement result of the detection level in the FPD 501b to the detection level sharing unit 601 of the FPD 501a via the I/F unit 201. The detection level sharing unit 601 of the FPD 501a inputs the received (obtained) measurement result of the detection level in the FPD 501b to the irradiation determination unit 206 in the FPD 501a.

The control unit 105b receives the measurement result of the detection level in the FPD 501a transmitted from the control unit 105a. Then, the control unit 105b transmits the received measurement result of the detection level in the FPD 501a to the detection level sharing unit 601 of the FPD 501b via the I/F unit 201. The detection level sharing unit 601 of the FPD 501b inputs the received (obtained) measurement result of the detection level in the FPD 501a to the irradiation determination unit 206 of the FPD 501b.

The FPD 501a and the FPD 501b perform the above-described processing operations in parallel. As a result, the measurement result of the detection level by the detection level measurement unit 205 of each FPD is shared between the plurality of FPDs (detection apparatuses).

Note that sharing processing by the detection level sharing units 601 is not limited to the above-described processing contents but can also be achieved by other methods. For example, each detection level sharing unit 601 can also be configured to have a wireless communication function. As another method, the detection level sharing units 601 of the respective FPDs can directly perform wireless communication to each other, and share the detection levels VSa and VSb.

Then, in step S705, the irradiation determination units 206 perform, based on the detection levels VSa and VSb, determination processing (presence/absence determination processing of radiation irradiation) of whether radiation is emitted from the radiation generator 101. As determination processing, the irradiation determination units 206 can perform determination processing that has been described in the first embodiment. If the sum of the radiation detection level measured in the first detection apparatus and the radiation detection level measured in the second detection apparatus exceeds a threshold, the irradiation determination units 206 determine the presence of radiation irradiation. As for the detailed contents of determination processing of determining, by the irradiation determination units 206, the absence of radiation irradiation if the sum of the detection levels becomes equal to or smaller than the threshold, the irradiation determination units 206 determine that there is radiation irradiation if the relationship of the sum of the detection levels (VSa+VSb)≥a thresholds VSth is satisfied, as described in the first embodiment. For example, as the plurality of detection apparatuses, the FPD 501a is used as the first detection apparatus and the FPD 501b is used as the second detection apparatus. If the sum of the radiation detection level (VSa) measured in the first detection apparatus and the radiation detection level (VSb) measured in the second detection apparatus exceeds the thresholds VSth, the irradiation determination units 206 determine the presence of radiation irradiation. On the other hand, if the sum of the detection levels (VSa+VSb) the thresholds VSth is obtained, the irradiation determination units 206 can determine that there is no radiation irradiation.

Figure 4:
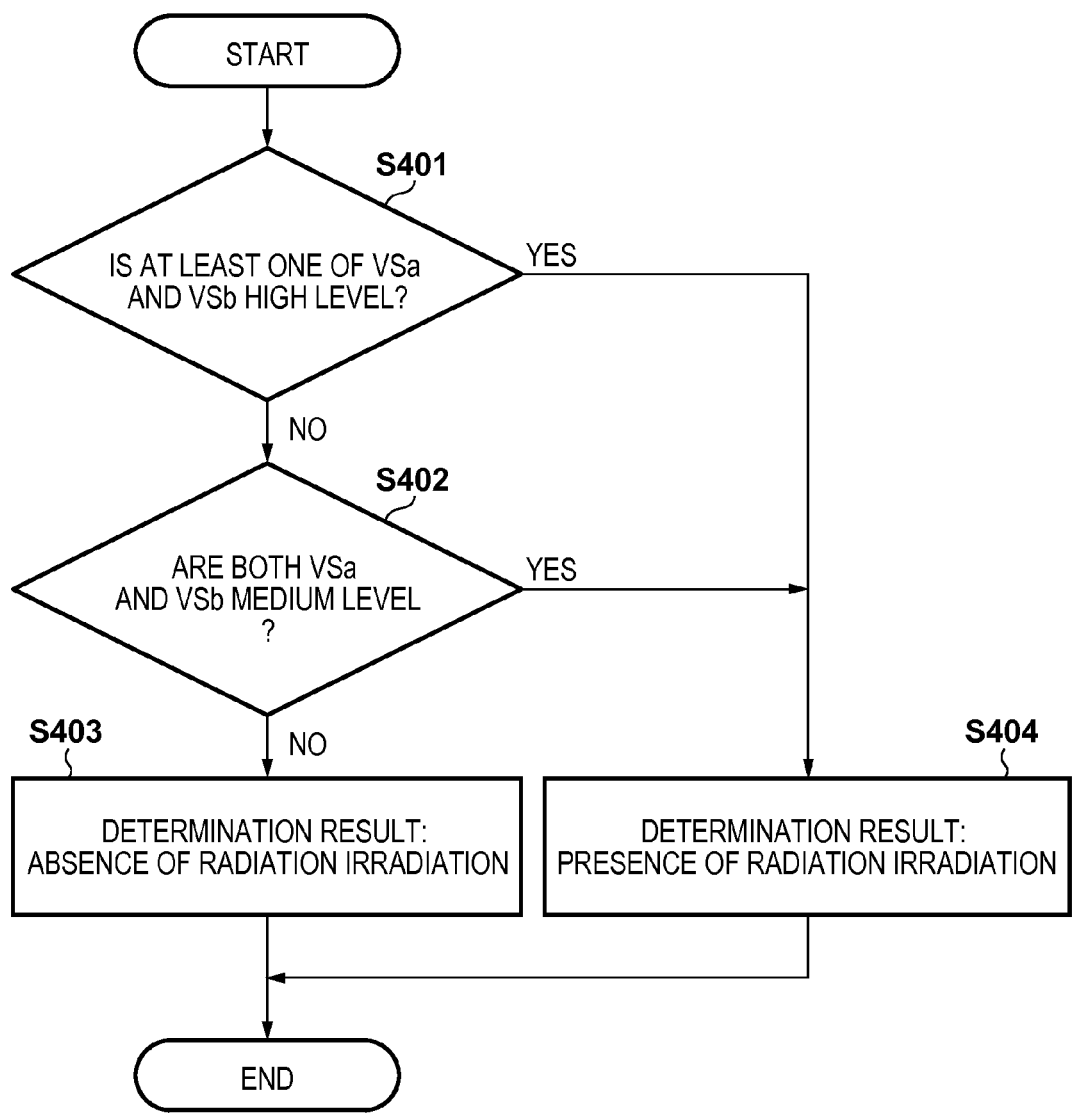
FIG. 4 is a flowchart for explaining a processing procedure of radiation irradiation determination.

Alternatively, the irradiation determination units 206 can determine the presence/absence of radiation irradiation in accordance with an algorithm described in FIG. 4. Note that the thresholds VSth include VSth1 (first threshold) and VSth2 (second threshold) smaller than the first threshold. The irradiation determination units 206 determine the presence of radiation irradiation if they determine that at least one of the radiation detection level measured in the first detection apparatus and the radiation detection level measured in the second detection apparatus exceeds the first threshold. Also, the irradiation determination units 206 determine the presence of radiation irradiation if both of the radiation detection level measured in the first detection apparatus and the radiation detection level measured in the second detection apparatus exceed the second threshold. Furthermore, the irradiation determination units 206 determine the absence of radiation irradiation if at least one of the radiation detection level measured in the first detection apparatus and the radiation detection level measured in the second detection apparatus becomes equal to or smaller than the second threshold.

For example, as the plurality of detection apparatuses, the FPD 501a is used as the first detection apparatus and the FPD 501b is used as the second detection apparatus. The irradiation determination units 206 determine the presence of radiation irradiation if they determine that at least one of the radiation detection level measured in the first detection apparatus and the radiation detection level measured in the second detection apparatus exceeds the first threshold (if it is high level (level HIGH)).

Alternatively, the irradiation determination units 206 determine the presence of radiation irradiation if both of the radiation detection level measured in the first detection apparatus and the radiation detection level measured in the second detection apparatus exceed the second threshold (if they are medium level (level MID)). In other words, the irradiation determination units 206 determine the presence of radiation irradiation if both of the radiation detection level measured in the first detection apparatus and the radiation detection level measured in the second detection apparatus exceed the second threshold simultaneously. The measurement units measure the radiation detection levels of the first detection apparatus and the second detection apparatus in a predetermined measurement cycle (for example, every 10 μsec). Within the period of this measurement cycle, if the radiation detection level measured in the first detection apparatus and the radiation detection level measured in the second detection apparatus exceed the second threshold, the irradiation determination units 206 determine the presence of radiation irradiation.

The irradiation determination units 206 determine the absence of radiation irradiation if one of the radiation detection level measured in the first measurement apparatus and the radiation detection level measured in the second detection apparatus becomes equal to or smaller than the second threshold (if it is low level (level LOW)). As described above, the presence/absence of radiation irradiation can also be determined in accordance with the algorithm described in FIG. 4.

Note that the presence/absence of radiation irradiation is determined using the first threshold and the second threshold in the above-described example. However, it can also be determined using only one threshold. The irradiation determination unit 206 may determine the presence of radiation irradiation if the detection level measured in each of the plurality of detection apparatuses exceeds a predetermined threshold. The predetermined threshold corresponds to VSth2 (second threshold). That is, the irradiation determination units 206 determine the presence of radiation irradiation if both of the radiation detection level measured in the first detection apparatus and the radiation detection level measured in the second detection apparatus exceed the predetermined threshold. Conversely, the irradiation determination units 206 determine the absence of radiation irradiation if one of the radiation detection level measured in the first detection apparatus and the radiation detection level measured in the second detection apparatus becomes equal to or smaller than the predetermined threshold.

Therefore, the irradiation determination units 206 determine the absence of radiation irradiation even if one of the detection apparatuses which detects radiation erroneously detects radiation. That is, it is possible to detect the presence/absence of radiation irradiation appropriately even if the detection apparatuses which detect radiation change locally due to an external environment. Note that the irradiation determination units 206 may determine the presence/absence of radiation irradiation by comparing the plurality of detection levels measured in the plurality of detection apparatuses with each other.

In step S706, each driving control unit 202 receives, from the irradiation determination unit 206, a result of presence/absence determination processing of radiation irradiation. Then, each driving control unit 202 changes control contents in accordance with the result of presence/absence determination processing. If each irradiation determination unit 206 determines the absence of radiation irradiation, each driving control unit 202 controls the measurement units to continue measurement of the radiation irradiation detection levels. Each driving control unit 202 returns processing to steps S703a and S703b, and continues measurement of the radiation irradiation detection levels (NO in step S706). If each irradiation determination unit 206 determines the absence of radiation irradiation, each driving control unit 202 controls the measurement units to continue measurement of the radiation irradiation detection levels. Then, in steps S703a and S703b, the measurement units (detection level measurement units 205) remeasure the radiation detection levels in the plurality of detection apparatuses.

Then, in steps S703a and S703b, the detection level measurement unit 205 of the FPD 501a and the detection level measurement unit 205 of the FPD 501b measure the radiation irradiation detection levels. Unless the presence of radiation irradiation is determined, the radiation imaging apparatus 500 repeats processing in steps S703a, S703b, S704, S705, and S706, and waits for radiation irradiation.

On the other hand, if the irradiation determination units 206 determine the presence of radiation irradiation in determination processing in step S706, the driving control units 202 advance processing to steps S707a and S707b (YES in step S706).

Image obtaining processing (image obtainment a) in step S707a is performed in the FPD 501a and image obtaining processing (image obtainment b) in step S707b is performed in the FPD 501b. In steps S707a and S707b, if the irradiation determination units determine the presence of radiation irradiation (YES in step S706), the plurality of detection apparatuses accumulate charges corresponding to radiation. The plurality of detection apparatuses start accumulating the charges corresponding to radiation simultaneously. Then, the plurality of detection apparatuses output image data, respectively, based on radiation. Furthermore, if each irradiation determination unit 206 determines the presence of radiation irradiation in the previous step S706, each driving control unit 202 performs control for obtaining, from the imaging unit, an image based on the accumulated charges. Note that processing operations in steps S707a and S707b are performed in parallel.

For example, in step S707a, the driving control unit 202 of the FPD 501a controls the A/D conversion unit 204 in order to obtain an image based on an electrical signal of the charges. The FPD 501a accumulates the charges corresponding to radiation. The A/D conversion unit 204 generates, under the control of the driving control unit 202, image data by reading out the charges accumulated in the solid-state image sensor of the imaging unit 203 as the electrical signal. The image data generated by the A/D conversion unit 204 is transmitted to the control unit 105a via the I/F unit 201. The control unit 105a saves the received image data in an image saving unit 107 or a RAM (not shown).

Likewise, in step S707b, the driving control unit 202 of the FPD 501b controls the A/D conversion unit 204 in order to obtain the image based on the electrical signal of the charges. The FPD 501b accumulates the charges corresponding to radiation. The A/D conversion unit 204 generates, under the control of the driving control unit 202, image data by reading out the charges accumulated in the solid-state image sensor of the imaging unit 203 as the electrical signal. The image data generated by the A/D conversion unit 204 is transmitted to the control unit 105b via the I/F unit 201. The control unit 105b saves the received image data in the image saving unit 107 or the RAM (not shown). With above-described processing, the images (image data) are obtained from the FPD 501a and the FPD 501b. That is, if the irradiation determination units 206 determine the presence of radiation irradiation, the plurality of detection apparatuses can accumulate the charges corresponding to radiation and output the image data, respectively, based on radiation.

More specifically, if the irradiation determination units 206 determine the presence of radiation irradiation, the plurality of detection apparatuses accumulate the charges corresponding to radiation. That is, the plurality of detection apparatuses start accumulating the charges corresponding to radiation simultaneously. The FPD 501a and the FPD 501b start accumulating the charges corresponding to radiation simultaneously. That is, charge accumulation is performed in cooperation with the plurality of detection apparatuses. Then, the plurality of detection apparatuses read out the accumulated charges as the electrical signals, and output the image data, respectively, based on radiation. Note that if the irradiation determination units 206 determine the absence of radiation irradiation, the plurality of detection apparatuses do not start accumulating the charges corresponding to radiation.

Furthermore, the irradiation determination units 206 determine the presence of radiation irradiation if they determine that at least one of the radiation detection level measured in the first detection apparatus and the radiation detection level measured in the second detection apparatus exceeds the first threshold. At this time, the first detection apparatus and the second detection apparatus start accumulating the charges corresponding to radiation simultaneously. Then, the first detection apparatus and the second detection apparatus can read out the accumulated charges as the electrical signals, and output the image data, respectively, based on radiation. Note that since the first threshold is a high-level threshold, there is a high probability of radiation irradiation. Therefore, for example, even if the irradiation determination units 206 determine that only the detection level measured in the first detection apparatus exceeds the first threshold (the detection level measured in the second detection apparatus does not exceed the first threshold), the first detection apparatus and the second detection apparatus output the image data, respectively, based on radiation.

Furthermore, the irradiation determination units 206 determine the presence of radiation irradiation if both of the radiation detection level measured in the first detection apparatus and the radiation detection level measured in the second detection apparatus exceed the second threshold simultaneously. Within the period of the measurement cycle of radiation detection, if the radiation detection level measured in the first detection apparatus and the radiation detection level measured in the second detection apparatus exceed the second threshold, the irradiation determination units 206 determine the presence of radiation irradiation. At this time, the first detection apparatus and the second detection apparatus start accumulating the charges corresponding to radiation simultaneously. Then, the first detection apparatus and the second detection apparatus can read out the accumulated charges as the electrical signals, and output the image data, respectively, based on radiation. Note that since the second threshold is a medium-level threshold, the probability of radiation irradiation is unknown. Therefore, if the irradiation determination units 206 determine that both of the radiation detection level measured in the first detection apparatus and the radiation detection level measured in the second detection apparatus exceed the second threshold, the first detection apparatus and the second detection apparatus output the image data, respectively, based on radiation. If the irradiation determination units 206 determine that one of the radiation detection level measured in the first detection apparatus and the radiation detection level measured in the second detection apparatus does not exceed the second threshold, neither the first detection apparatus nor the second detection apparatus outputs the image data based on radiation.

Note that it is also possible to re-set the predetermined threshold (the medium-level threshold or the second threshold) based on the determination result by each irradiation determination unit 206. The irradiation determination units 206 determine the absence of radiation irradiation if they determine that only the detection level measured in the first detection apparatus exceeds the predetermined threshold and the detection level measured in the second detection apparatus does not exceed the predetermined threshold. That is, the first detection apparatus regards it as a radiation detection error. Therefore, in order to avoid the radiation detection error by the first detection apparatus, each irradiation determination unit 206 re-sets the predetermined threshold such that the detection level detected by the first detection apparatus does not exceed the predetermined threshold. Note that re-set threshold is also applied to the second detection apparatus. It is therefore possible to reduce radiation detection errors by the first detection apparatus and the second detection apparatus.

In step S708, the image generating unit 502 of the image processing unit 108 combines the plurality of images (image data) generated by the A/D conversion units 204 of the plurality of FPDs (detection apparatuses) to generate one image (image data). The image generating unit 502 combines the images (image data) obtained from the FPD 501a and the FPD 501b which are saved in the image saving unit 107 or the RAM (not shown) together to generate one image (image data). A generation method by combination can be implemented by, for example, an image processing technique called stitching which is generally used for long-object imaging or the like. The image generating unit 502 stores the generated image (image data) in the image saving unit 107 or the RAM in a manner similar to that for the other image.

Next, in step S709, the image processing unit 108 performs image processing on the images (image data) stored in the image saving unit 107 or the RAM. The pre-processing unit 115 of the image processing unit 108 can perform, for example, pre-processing such as offset correction, sensitivity correction, pixel correction, and the like to correct characteristic variations in the solid-state image sensor of each FPD. Further, the diagnosis image processing unit 116 can perform diagnosis image processing such as tone processing, dynamic range processing, spatial frequency processing, and the like.

Then, in step S710, the display unit 110 displays, on a monitor, the images (image data) which have undergone image processing by the image processing unit 108. Then, processing in the radiation imaging apparatus 500 ends.

Third Embodiment

It is also possible to arrange each FPD that has been described in the first embodiment and the second embodiment as a detection apparatus which detects radiation. In this case, for example, a detection unit (FPD 102) which detects radiation includes an imaging unit 203 which outputs charge information corresponding to radiation, as shown in FIG. 2. The detection unit (FPD 102) also includes measurement units (detection level measurement units 205a and 205b) which measure, using the charge information, radiation detection levels in the different regions of the imaging unit 203. The detection apparatus (FPD 102) further includes an irradiation determination unit 206 which determines the presence/absence of radiation irradiation by comparing a threshold and the measured detection levels.

Alternatively, as shown in FIG. 6, each of detection apparatuses (FPDs 501a and 501b) which detects radiation includes the imaging unit 203 which outputs the charge information corresponding to radiation. Each of the detection apparatuses (FPDs 501a and 501b) also includes a measurement unit (detection level measurement unit 205) which measures the radiation detection level using the charge information. Each detection apparatus further includes a detection level sharing unit 601 which obtains the radiation detection level measured in the other detection apparatus, and the irradiation determination unit 206 which determines the presence/absence of radiation irradiation by comparing the threshold, and the measured detection level and the obtained detection level.

The embodiments of the present invention have been described above. However, the present invention is not limited to these embodiments, and various modifications and changes can be made within the scope of the invention. According to each embodiment described above, it becomes possible for the detection apparatus which detects radiation to detect the presence/absence of radiation irradiation appropriately even if it changes locally due to an external environment. It becomes possible to detect the presence/absence of radiation irradiation appropriately even if detection of local radiation irradiation, or a change in the characteristics of the detection apparatus, external noise, physical impact, or the like that has generated locally may occur. According to each embodiment described above, it becomes possible to detect the presence/absence of radiation irradiation appropriately even if the external environment changes locally.

According to the embodiments of the present invention, it becomes possible to detect the presence/absence of radiation irradiation appropriately even if the external environment changes locally.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-102727, filed May 16, 2014, and Japanese Patent Application No. 2015-002598, filed Jan. 8, 2015 which are hereby incorporated by reference herein in their entirety.

What is claimed is:

1. A radiation imaging apparatus which includes a plurality of flat panel detectors configured to output image data based on an irradiated radiation, the apparatus comprising:
a measurement unit configured to measure radiation detection levels in the plurality of flat panel detectors;
an irradiation determination unit configured to determine irradiation or non-irradiation of a radiation based on the radiation detection levels measured in at least one of the plurality of flat panel detectors; and
an image generating unit configured to combine a plurality of image data output from the plurality of flat panel detectors to generated one image data,
wherein the plurality of flat panel detectors detect irradiated radiation and output the image data based on the irradiated radiation in a case that the irradiation determination unit determines the irradiation of the radiation.

2. The apparatus according to claim 1, wherein the irradiation determination unit determines the presence of radiation irradiation if the respective radiation detection levels measured in the plurality of flat panel detectors exceed a predetermined threshold.

3. The apparatus according to claim 2, wherein the irradiation determination unit determines the irradiation or non-irradiation of the radiation by comparing the plurality of radiation detection levels measured in the plurality of flat panel detectors with each other.

4. The apparatus according to claim 1, wherein the irradiation determination unit determines the presence of radiation irradiation if both of the radiation detection level measured in a first detection apparatus and the radiation detection level measured in a second detection apparatus exceed a predetermined threshold.

5. The apparatus according to claim 1, wherein the irradiation determination unit determines the absence of radiation irradiation if one of the radiation detection level measured in a first detection apparatus and the radiation detection level measured in a second detection apparatus becomes not more than a predetermined threshold.

6. The apparatus according to claim 1, further comprising a detection level sharing unit configured to obtain and share the radiation detection level measured in a first detection apparatus and the radiation detection level measured in a second detection apparatus,
wherein the irradiation determination unit determines the irradiation or non-irradiation of the radiation by comparing a threshold and the shared respective radiation detection levels.

7. The apparatus according to claim 6, wherein the irradiation determination unit
determines the presence of radiation irradiation if a sum of the radiation detection level measured in the first detection apparatus and the radiation detection level measured in the second detection apparatus exceeds the threshold; and determines the absence of radiation irradiation if the sum of the radiation detection levels becomes not more than the threshold.

8. The apparatus according to claim 6, wherein the threshold includes a first threshold and a second threshold smaller than the first threshold, and the irradiation determination unit determines the presence of radiation irradiation if at least one of the radiation detection level measured in the first detection apparatus and the radiation detection level measured in the second detection apparatus exceeds the first threshold, determines the presence of radiation irradiation if both of the radiation detection level measured in the first detection apparatus and the radiation detection level measured in the second detection apparatus exceed the second threshold, and determines the absence of radiation irradiation if at least one of the radiation detection level measured in the first detection apparatus and the radiation detection level measured in the second detection apparatus becomes not more than the second threshold.

9. The apparatus according to claim 1, further comprising a driving control unit configured to control, in accordance with a determination result by the irradiation determination unit, an imaging unit configured to output charge information corresponding to radiation.

10. The apparatus according to claim 9, wherein if the irradiation determination unit determines the presence of radiation irradiation, the driving control unit performs control for obtaining an image based on accumulated charges from the imaging unit.

11. The apparatus according to claim 9, wherein if the irradiation determination unit determines the absence of radiation irradiation, the driving control unit controls the measurement units to continue measurement of radiation irradiation detection levels.

12. The apparatus according to claim 1, wherein if the irradiation determination unit determines the presence of radiation irradiation, the plurality of flat panel detectors accumulate charges corresponding to radiation.

13. The apparatus according to claim 1, wherein if the irradiation determination unit determines the presence of radiation irradiation, the plurality of flat panel detectors start accumulating charges corresponding to radiation simultaneously.

14. The apparatus according to claim 1, wherein if the irradiation determination unit determines the presence of radiation irradiation, the plurality of flat panel detectors output image data, respectively, based on radiation.

15. The apparatus according to claim 1, wherein if the irradiation determination unit determines the absence of radiation irradiation, the measurement unit re-measures the radiation detection levels in the plurality of flat panel detectors.

16. A method of determining radiation irradiation in a radiation imaging apparatus which includes a plurality of flat panel detectors configured to output image data based on an irradiated radiation, the method comprising:

measuring radiation detection levels in the plurality of flat panel detectors;

determining irradiation or non-irradiation of a radiation based on the radiation detection levels measured in at least one of the plurality of flat panel detectors; and combining a plurality of image data output from the plurality of flat panel detectors to generate one image data, wherein the plurality of flat panel detectors detect the irradiated radiation and output the image data based on the irradiated radiation in a case that the irradiation of the radiation is determined.

17. A non-transitory computer-readable storage medium storing a program that causes a computer to execute a method of determining radiation in a radiation imaging apparatus which includes a plurality of flat panel detectors configured to output image data based on an irradiated radiation, the method comprising:

measuring radiation detection levels in the plurality of flat panel detectors;

determining irradiation or non-irradiation of a radiation based on the radiation detection levels measured in at least one of flat panel detectors; and combining a plurality of image data output from the plurality of flat panel detectors to generate one image data, wherein the plurality of flat panel detectors detect the irradiated radiation and output the image data based on the irradiated radiation in a case that the irradiation of the radiation is determined.

18. A radiation imaging apparatus which includes a plurality of flat panel detectors configured to output image data based on an irradiated radiation, the apparatus comprising:

an irradiation determination unit configured to determine irradiation or non-irradiation of a radiation in each of flat panel detectors; and an image generating unit configured to generate one image data based on a plurality of image data output by the plurality of flat panel detectors, wherein each of the plurality of flat panel detectors detects the irradiated radiation and outputs the image data based on the irradiated radiation, and the image generating unit generates one image data by combining the plurality of image data output by the plurality of flat panel detectors in a case that the irradiation determination unit determines the irradiation of the radiation.

19. A method of determining radiation irradiation in a radiation imaging apparatus which includes a plurality of flat panel detectors configured to output image data based on an irradiated radiation, the method comprising:

determining irradiation or non-irradiation of a radiation in each of flat panel detectors; and generating one image data based on a plurality of image data output by the plurality of flat panel detectors, wherein each of the plurality of flat panel detectors detects the irradiated radiation and outputs the image data based on the irradiated radiation, and one image data is generated by combining a plurality of image data output by the plurality of flat panel detectors in a case that the irradiation of the radiation is determined.

20. A non-transitory computer-readable storage medium storing a program that causes a computer to execute a method of determining radiation irradiation in a radiation imaging apparatus which includes a plurality of flat panel detectors configured to output image data based on an irradiated radiation, the method comprising:

determining irradiation or non-irradiation of a radiation in each of flat panel detectors; and generating one image data based on a plurality of image data output by the plurality of flat panel detectors, wherein each of the plurality of flat panel detectors detects the irradiated radiation and outputs the image data based on the irradiated radiation, and one image data is generated by combining the plurality of image data output by the plurality of flat panel detectors in a case that the irradiation of the radiation is determined.

21. A radiation imaging apparatus which includes a plurality of flat panel detectors configured to output image data based on an irradiated radiation, the apparatus comprising:
an irradiation determination unit configured to determine irradiation or non-irradiation of a radiation in each of flat panel detectors; and
an image generating unit configured to generate one image data based on a plurality of image data output by the plurality of flat panel detectors,
wherein the plurality of flat panel detectors, which were determined as the irradiation by the irradiation determination unit, independently output the image data based on the irradiated radiation, and the image generating unit generates one image data by combining the plurality of image data output by the plurality of flat panel detectors.

22. A method of determining radiation irradiation in a radiation imaging apparatus which includes a plurality of flat panel detectors configured to output image data based on an irradiated radiation, the method comprising:
determining irradiation or non-irradiation of a radiation in each of flat panel detectors; and
generating one image data based on a plurality of image data output by the plurality of flat panel detectors,
wherein the plurality of flat panel detectors, which were determined as the irradiation in the determining step, independently output the image data based on the irradiated radiation, and one image data is generated by combining the plurality of image data output by the plurality of flat panel detectors in the generating step.

23. A non-transitory computer-readable storage medium storing a program that causes a computer to execute a method of determining radiation irradiation in a radiation imaging apparatus which includes a plurality of flat panel detectors configured to output image data based on an irradiated radiation, the method comprising:
determining irradiation or non-irradiation of a radiation in each of flat panel detectors; and
generating one image data based on a plurality of image data output by the plurality of flat panel detectors,
wherein the plurality of flat panel detectors, which were determined as the irradiation in the determining step, independently output the image data based on the irradiated radiation, and one image data is generated by combining the plurality of image data output by the plurality of flat panel detectors in the generating step.

* * * * *